United States Patent [19]

Sivaramakrishnan et al.

[11] Patent Number: 5,219,572
[45] Date of Patent: Jun. 15, 1993

[54] CONTROLLED RELEASE DELIVERY DEVICE FOR MACROMOLECULAR PROTEINS

[75] Inventors: Kallidaikurichi N. Sivaramakrishnan; Lindy F. Miller, both of Terre Haute, Ind.

[73] Assignee: Pitman-Moore, Inc., Mundelein, Ill.

[21] Appl. No.: 734,120

[22] Filed: Jul. 25, 1991

Related U.S. Application Data

[63] Continuation of Ser. No. 324,740, Mar. 17, 1989, abandoned.

[51] Int. Cl.$^5$ .............................................. A23K 1/18
[52] U.S. Cl. ................................ 424/438; 424/484; 424/464; 424/489; 424/490
[58] Field of Search ............... 424/455, 458, 459, 460, 424/438

[56] References Cited

U.S. PATENT DOCUMENTS

| | | | |
|---|---|---|---|
| 3,247,066 | 4/1966 | Milosovich | 424/456 |
| 4,177,256 | 12/1979 | Michaels et al. | 424/22 |
| 4,196,187 | 4/1980 | Dannelly et al. | 424/482 |
| 4,842,863 | 6/1989 | Nishimura et al. | 424/438 |
| 4,894,234 | 1/1990 | Sharma et al. | 424/440 |
| 4,975,280 | 12/1990 | Schect et al. | 424/425 |

OTHER PUBLICATIONS

Ueda et al., Design and Development of Time-Controlled Explosion System (TES) as a Controlled Drug Release System, *Proceed. Intern. Symp. Control. Rel. Bioact. Mater.* 15, 1988, Controlled Release Society, Inc. discloses an oral controlled drug release system which contains a drug and a swelling agent and is coated with a water-insoluble polymer, The device releases the drug after a "lag time", which depends upon the thickness of the membrane, The osmotic agent (sucrose bead), drug, swelling agent and polymer membrane are arranged on concentric layers to produce the bead.

*Primary Examiner*—Thurman K. Page
*Assistant Examiner*—Leon R. Horne
*Attorney, Agent, or Firm*—Wendell R. Guffey; William J. Fisher

[57] ABSTRACT

A controlled release delivery device for macromolecular proteins which comprises a water-soluble outer capsule completely surrounding an inner compartment containing a plurality of non-uniform beadlets. The beadlets comprise a rupturable wax shell which completely surrounds a core matrix containing the macromolecular proteins and optional "core agents" such as excipients, stabilizers, binders, surfactants, preservatives, or mixtures thereof, and the like.

The water-soluble outer capsule dissolves when the device is administered to an animal and simultaneously exposes substantially all of the beadlets to an aqueous environment. Each beadlet absorbs fluid from the environment and separately ruptures over a prolonged period thus delivering the macromolecular protein to the animal.

23 Claims, 2 Drawing Sheets

Fig. 2

CONTROLLED RELEASE DELIVERY DEVICE FOR MACROMOLECULAR PROTEINS

This application is a continuation of application Ser. No. 324,740, filed Mar. 17, 1989 now abandoned.

This invention relates generally to controlled release delivery devices and particularly to a controlled release delivery device for the prolonged release of macromolecular proteins.

BACKGROUND OF THE INVENTION

The delivery of macromolecular proteins to animals is complicated by the need for delivery devices which will maintain the bioactivity of the protein prior to, during, and after administration to the animal. Merely exposing macromolecular proteins to aqueous environments causes the large proteins to form precipitates and aggregates which destroy the bioactivity and therefore the usefulness of the protein. Also, hydrolytic reactions resulting from "wetting" the proteins may produce bio-inactive products which reduce the in vivo effectiveness of the protein.

Prior art methods for overcoming this problem have included encapsulating the macromolecular proteins in polymer-coated tablets which limit the ingress of water, pressing the macromolecular proteins into pellet compositions which control the release of the protein by limiting the surface area of the pellet and therefore the amount of water that has access to the protein, placing the macromolecular proteins in porous devices which limit the ability of water to enter the device and the ability of the protein to exit the device, and the like. Patents and other references describing these methods are voluminous and well known in the art.

Prior art particularly relevant to the present invention include U.S. Pat. No. 4,177,256 which discloses a drug delivery device in which discrete depots containing an osmotic solute are dispersed in a polymer body such that the polymer completely surrounds the depots. The polymer body is formed such that the defined surface area that is exposed to the environment is controlled. Water enters the polymer at the surface, saturates the depots, and generates an osmotic pressure within the depots which causes them to burst and release their contents to the environment. Only the depots near the surface are affected initially; the water penetrates the polymer body over time and ruptures depots that are encased deeper in the body. The prolonged release is achieved by the size and shape of the polymeric body; by controlling the surface area and the time it takes the water from the environment to reach the depots. The depots are uniform in size and composition and rupture within a relatively short time after being exposed to the water.

U.S. Pat. No. 3,247,066 discloses a water-soluble beadlet which comprises a core of medicant surrounded by a water-permeable polymer coating. When the beadlet is placed in an aqueous environment, water enters the beadlet and causes the core to expand. The expanding core "bursts" the coating and releases the medicant in the core. The beadlet is designed to be used within the gastrointestinal tract, have a release time of 8-12 hours, and is designed to deliver low molecular weight organics, antibiotics, and the like, particularly compounds such as aspirin, barbiturates, and similar low molecular weight organic molecules. Additionally, a preferred embodiment of the disclosed invention comprises a plurality of small beads having different surface areas, coating thicknesses, coating types, and the like which are administered in a pharmaceutical carrier such as a soft shelled capsule. The invention is not, however, designed to deliver macromolecular proteins for prolonged periods via a non-gastrointestinal route.

Ueda et al., Proceed. Intern. Symp. Control. Rel. Bioact. Mater., Vol. 15, page 450 (1988) disclose a time-controlled explosion system (TES) for delivering drugs in vivo. Ueda states that any pattern of drug release can be obtained by combining spheres with different coating thicknesses. However, Ueda's TES system is not designed to meet the special requirements for delivering macromolecular proteins. Also, Ueda's device has an "onion-like" structure; a sucrose bead is surrounded by the drug, the drug-bead is surrounded by a swelling agent, and the drug-bead-swelling agent is surrounded by a polymer.

Because of the problems associated with prior controlled release delivery devices for macromolecular proteins, there exists a continuing need for new controlled release delivery devices which control the manner and timing of delivery while maintaining the stability and bioactivity of the macromolecular proteins when the device is administered to an animal.

SUMMARY OF THE INVENTION

It is, therefore, an object of the present invention to provide a controlled release delivery device for macromolecular proteins.

It is another object of the present invention to provide a controlled release delivery device for macromolecular proteins which controls the manner and timing of delivery while maintaining the stability and bioactivity of the macromolecular proteins.

These and other objects are achieved using a controlled release delivery device for macromolecular proteins which comprises a water-soluble outer capsule completely surrounding an inner compartment containing a plurality of non-uniform beadlets. The beadlets comprise a rupturable wax shell which completely surrounds a core matrix containing the macromolecular proteins and optional "core agents" such as excipients, stabilizers, binders, surfactants, preservatives, or mixtures thereof, and the like.

When administered to an animal, the water-soluble outer capsule dissolves in a relatively short time, typically 1-6 hours, and simultaneously exposes substantially all of the beadlets to an aqueous environment. Each beadlet absorbs fluid from the environment and separately ruptures over a prolonged period. The time required for rupture depends upon the characteristics of the wax shell and the core matrix. As the beadlets rupture, the macromolecular protein contained in the matrix is delivered to the animal.

Other objects, advantages, and novel features of the present invention will become apparent from the following detailed description of the invention.

DETAILED DESCRIPTION OF THE INVENTION

The present invention is a controlled release delivery device for delivering macromolecular proteins to an animal over a prolonged period which comprises a water-soluble outer capsule completely surrounding an inner compartment containing a plurality of non-uniform beadlets designed to rupture periodically over a prolonged period. The beadlets comprise a rupturable wax shell which completely surrounds a core matrix containing a macromolecular protein and optional "core agents" such as excipients, stabilizers, binders, surfactants, preservatives, or mixtures thereof, and the like.

When implanted in the animal, the outer capsule dissolves in about 1-6 hours thereby exposing the beadlets directly to body fluids. Each beadlet separately ruptures over a prolonged period depending upon shell and matrix core parameters; the rupturing of the shell delivers the macromolecular protein contained in the beadlet to the body.

Figure 1:
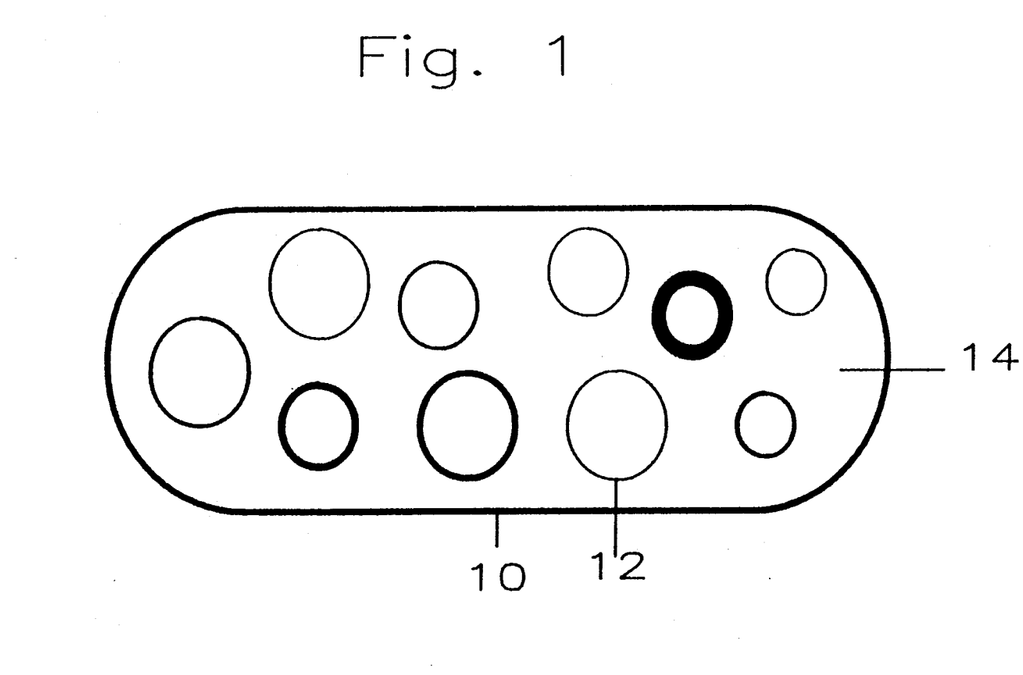
FIG. 1 shows one embodiment of the controlled release delivery device according to the present invention.
Figure 2:
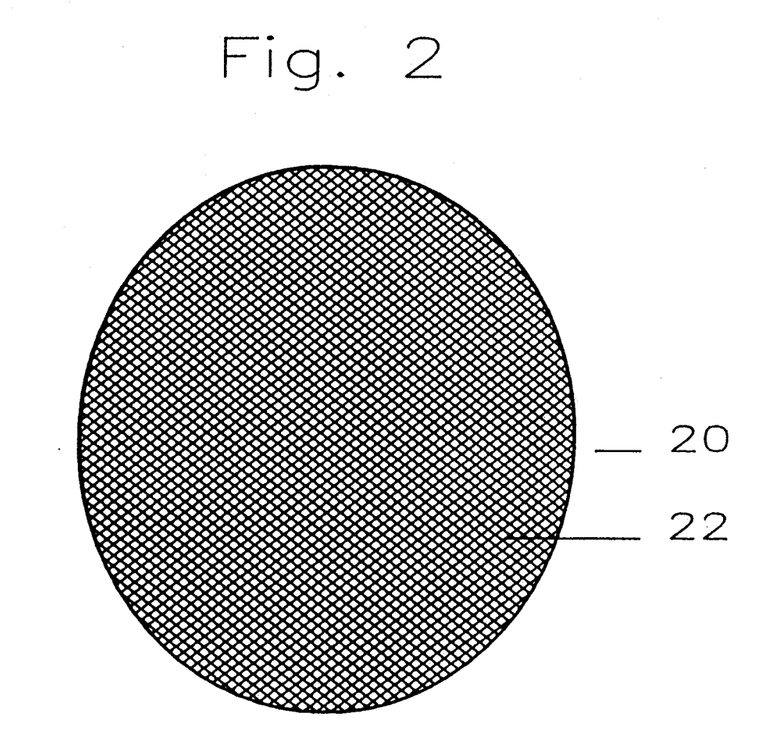
FIG. 2 shows one embodiment of the beadlets according to the present invention.

Referring to FIGS. 1 and 2 as illustrative examples of the present invention, the controlled release delivery device shown in FIG. 1 comprises a water-soluble outer capsule 10 completely surrounding an inner compartment 14 containing a plurality of non-uniform beadlets 12. Referring to FIG. 2, the beadlets (shown as 12 in FIG. 1) comprise a rupturable wax shell 20 which completely surrounds a core matrix 22 containing the macromolecular protein and optional core agents.

The beadlet of the present invention can be formed by any procedure which provides (1) an essentially uniform core matrix containing the macromolecular protein and optional core agents, (2) an essentially uniform wax shell and (3) which is non-destructive to the macromolecular protein; several such methods are known in the art. However, formation of beadlets containing macromolecular proteins poses particular problems not addressed in the prior art. Macromolecular proteins lose their bioactivity when exposed to harsh environmental conditions such as high or low pH or high temperatures. In addition, exposure of the protein to organic solvents may change the conformation and destroy the bioactivity of the protein. Methods such as many of those disclosed in the prior art, particularly U.S. Pat. No. 3,247,066, may not be useful to produce the present beadlets. In particular, those methods which use organic solvents and high temperatures may destroy the bioactivity of the present protein.

The beadlets of the present invention are preferably microcapsules, tablets or pellets. Pellets and tablets useful in the present device can be formed, for example, by the compression of dry powders to produce small pellets having sizes ranging from about 1 to 5 mm. Alternatively, a mixture of protein and core agents are moistened with a suitable liquid such as water or buffer solution and subsequently molded or extruded to yield small pellets. This technique can be modified to give spherical pellets suitable for further coating with wax as described herein.

Microcapsules can be produced by techniques such as spray-drying, spray-congealing, spray-chilling, and other well known methods. For example, the macromolecular protein and other optional core agents may be incorporated in molten wax or mixtures thereof and then forming microcapsules of the resulting mixture by a variety of techniques such as emulsifying or atomizing the mixture or by processing the mixture of ingredients and molten wax or mixtures thereof, mechanically and cooling. Alternatively, a mixture of the macromolecular proteins and core agents and wax or mixtures thereof may be cooled to give a solid which may then be processed by procedures such as milling, grinding, and the like. Microcapsules may be produced using these methods which have a diameter from about 1-1,500 microns. However, the average diameter is preferably from about 50-1000 microns.

A broad overview of these techniques may be found in Chapter 89, p.1553-1584 of Remington's Pharmaceutical Sciences, 16th edition (1980), Mack Publishing Company, Easton, Pa. 18042.

To produce the device of the present invention, beadlets must be made which are non-uniform with respect to the parameters which affect the rupture time. This may require producing several batches of beadlets and blending and mixing these non-uniform beadlets to produce the present device.

Parameters that affect the rupturing of the beadlet include, but are not limited to, (1) permeability of the wax shell to water, (2) shell thickness, (3) porosity of the shell, (4) type and chemical structure of the wax comprising the shell, (5) strength or toughness of the shell, (6) the osmotic pressure developed by the core matrix, and (7) the loading of the macromolecular proteins in the core matrix.

Generally, macromolecular proteins suitable for inclusion in the core matrix and thus deliverable in the controlled release delivery device of the present invention include but are not limited to proteins having a molecular weight from about 2000 to about 200,000 daltons. The macromolecular proteins include but are not limited to natural, recombinant, synthetic and mutein proteins which have deleted, inserted, substituted, or otherwise modified sequences and biologically active fragments and derivatives thereof. More specifically, bioactive proteins such as enzymes, enzyme inhibitors, antibodies, antigens, interferons, insulins, prolactins, somatomedins, somatostatins, interleukins, somatocrinins (GRF) and somatotropins can be delivered according to the present invention.

Particularly, human, porcine, bovine, equine, ovine, and avian somatotropins can be delivered using the controlled release delivery devices of the present invention. Somatotropin is defined herein to include all proteins having somatotropin activity including the natural, recombinant, synthetic, and mutein somatotropins having deleted, inserted, substituted, or otherwise modified sequences and biologically active fragments and derivatives thereof. Additionally, metals or metal compounds associated with biologically active proteins, peptides and polypeptides, as well as acid salts, derivatives and complexes and antihydrating agents are suitable for incorporation into the controlled release delivery device of the invention.

Somatotropins useful in the present invention can be obtained from any suitable source. Methods for producing, isolating and purifying native and recombinant somatotropins are well known in the art. The amino acid sequences of various somatotropins useful in the present invention are well known: C. H. Li in Kirk-Othmer "Encyclopedia of Chemical Technology", 3rd E., Vol. 12, pp. 549-552 (human somatotropin), R. P. Woychik, *Nucleic Acid Res.*, 10, 7197 (1982) (bovine somatotropin), C. H. Li et al., *Arch. Biochem. Biophys.*, 156, 493-508 (1973) (ovine somatotropin) and P. H.

Seeburg et al., *DNA*, 2, 37, 45 (1983) (porcine somatotropin), all incorporated herein by reference.

The macromolecular proteins should comprise from about 1–70% by weight of the beadlet, preferably from about 5–50%.

Core agents such as excipients, stabilizers, binders, preservatives, surfactants and the like suitable for inclusion in the core matrix include arginine, arginine hydrochloride, glycine, ethylenediamine tetraacetic acid (EDTA), salts, lysine, magnesium stearate, sucrose, and the like. Preferred preservatives include salicylanilide, sorbic acid, boric acid, benzoic acid, and salts thereof. The core agents should comprise from about 30–99% by weight of the beadlet, preferably from about 50–90%.

Waxes useful for producing the beadlet's rupturable wax shell include animal waxes such as beeswax, lanolin, shellac wax, and Chinese insect wax, vegetable waxes such as hydrogenated soybean oil, cottonseed oil, carnauba, candelilla, bayberry, and sugar cane, and mineral waxes such as fossil or earth waxes (ozocerite, ceresin, montan) and petroleum waxes (paraffin, microcrystalline, slack or scale wax), or combinations thereof. Preferably the wax material used in the present invention is beeswax, vegetable wax, carnauba wax, or combinations thereof.

The rupturable wax shell may be formed with a film modifying agent to provide the desired degree of water-permeability in the finished shell. Among the many substances which may be used are modifying agents such as polyethylene glycol, polypropylene glycol, glycerol esters, particularly ethoxylated esters of glycerol such as "Mazol" (Mazol is a mixture of partially alkoxylated mono- and diglycerides), Pluronics, waxes, oils, and the like.

The rupturable wax shell should comprise from about 5–40% by weight of the beadlet, preferably from about 10–30%.

The water-soluble capsule can be formed from any material which dissolves in a relatively short period, preferably 1–6 hours, and is biocompatible and compatible with the beadlet wax shell containing the macromolecular protein. Preferably the capsule material is selected from polyvinylpyrrolidine, hydroxypropylmethyl cellulose, gelatin, hydroxypropyl cellulose, and soluble glasses. Most preferably, the capsule material is hydroxypropyl cellulose or gelatin.

The water-soluble capsule should comprise from about 1–30% by weight of the device, preferably from about 5–20%.

The controlled release delivery device of the present invention is produced by encapsulating a plurality of non-uniform beadlets containing the macromolecular protein and optional agents in a water-soluble capsule using methods well known in the art. For example, the device can be produced from a standard gelatin capsule using an operation requiring only three separate steps: (1) separation of the top half (cap) of the capsule; (2) filling of the bottom half (body) of the capsule, and (3) rejoining of the cap and the body. This sequence of operations can be performed with semi-automatic or fully automated capsule-filling machines known in the art and widely used in the pharmaceutical industry. Such machines are capable of filling powders, tablets, microcapsules, or pellets into capsules. A description of equipment suitable for this purpose may be found in Chapter 89, p. 1577 ff, of Remington's Pharmaceutical Sciences, 16th edition (1980), Mack Publishing Company, Easton, Pa. 18042.

When the device of the present invention is administered to an animal, the water-soluble outer capsule dissolves in a relatively short time, typically 1–6 hours, and simultaneously exposes substantially all of the beadlets to an aqueous environment. Each beadlet separately ruptures over a prolonged period; the time required for each beadlet to rupture depends upon the parameters and characteristics of the shell and the core matrix. Generally, the rupture time for each beadlet is controlled by varying the type, thickness and porosity of the wax shell and by selecting the compounds in the core matrix to control the osmolality and the rate at which water will penetrate the shell. Obviously, the faster the water enters the beadlet the sooner the shell will rupture. Therefore, beadlets with a thin shell, a matrix having a high osmotic pressure, or a relatively high water-permeable shell will rupture and deliver the protein within a relatively short time after being exposed to an aqueous environment. Other beadlets having a matrix with a lower osmotic pressure or thicker or less water-permeable shell will remain intact for a prolonged period and will rupture at various times depending upon the characteristics of the particular shell and matrix. This method provides delivery of the macromolecular proteins over the life of the device; somewhat similar to a series of injections. By varying the characteristics of the beadlets, the macromolecular proteins can be delivered to the animal at desired intervals (hours or days). This latter method eliminates the need for multiple administrations to the animal; one implanted device can replace several injections.

A sufficient number of beadlets having different rupture time parameters should be incorporated into the device to insure delivery of the macromolecular protein to the animal in the required dosages.

For the administration of somatotropin, beadlets having shell parameters which vary the rupture times uniformly over a period of from about 1–14 days are produced. The beadlets have a size of from about 50–1000 microns and comprises from about 1–70% somatotropin and up to about 65% core agents. Similarly, pellets have a size of from about 1–5 mm and comprises from about 1–70% somatotropin and up to about 65% core agents. A mixture of beadlets designed to deliver from about 0.1–20 mg/animal/day, preferably from about 1–10 mg/animal/day, over a period of from about 1–14 days is incorporated into the outer capsule of the present invention. The resulting device can be implanted into an animal to promote growth and increase feed utilization efficiency.

Preferably, the core matrix comprises a mixture of somatotropin, arginine, and sucrose (1/3/1 parts by weight); the wax shell comprises a 80/20/2 (parts by weight) mixture of beeswax carnauba wax, and Mazol; and the outer capsule comprises hydroxypropyl cellulose or gelatin.

According to the present invention, a method for delivering macromolecular proteins to an animal comprises administering to the animal the controlled release delivery device of the present invention. The outer capsule dissolves in about 1–6 hours thereby exposing the beadlets directly to body fluids. Each beadlet separately ruptures over a prolonged period depending upon the wax shell's parameters such as thickness, type, and the like. Ideally, beadlets with a thin shell or a relatively high water-permeable shell undergo rupture at an early stage and deliver the protein immediately. Other beadlets having a thicker or less water-permeable shell remain intact for a prolonged period and undergo rupture at various times depending upon the characteristics of the particular shell. This method provides delivery of the protein over the life of the implant; somewhat similar to a series of injections.

In another aspect of the present invention, a method for promoting growth and increasing feed utilization efficiency in an animal over a prolonged period comprises administering to an animal the device of the present invention containing somatotropin as the macromolecular protein. The somatotropin should be present in the beadlets of the controlled release delivery device in an amount effective to promote growth when administered to the animal. Although the amount of somatotropin required to promote growth may vary depending upon the particular somatotropin, the type of animal, and the desired results, the somatotropin is generally present in amounts from about 1-70% by weight of the beadlet in the delivery device, preferably from about 5-50%. Somatotropin is typically administered to animals in dosages from about 0.1-20 mg/animal/day, preferably from about 1-10 mg/animal/day to promote growth and increase feed utilization efficiency.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

A zinc complex of recombinant porcine somatotropin (Zn-rpST), arginine, and sucrose (1/3/1 parts by weight) were mixed in a Vortex shaker. The size of the particles was kept at less than 250 microns. A three-layer tablet was made as follows from this mixture and powdered carnauba wax. Carnauba wax (15 mg) was placed in the die of a single station Key tablet press, followed by 50 mg of the Zn-rpST-matrix and another 15 mg of carnauba wax. Compression was effected in a single sweep to produce a three-layer pellet consisting of a Zn-rpST-matrix flanked by two layers of wax. Concave punches were used so as to produce convex pellets. The pellets were held at the tip of a needle connected to a vacuum source and dipped for about one second in a molten mixture of beeswax, carnauba wax, and Mazol (80/20/2 parts by weight) kept at about 85° C. The mean percent coating weight (i.e. the ratio of the coating weight to the weight of uncoated pellet) for a set of 8 pellets was 16.7±1.9. The coated pellets were placed in 8 ml of Phosphate Buffered Saline (PBS; 10 mM; pH 7.4) and shaken in a water-bath at 37° C. They were checked periodically for any visible changes such as rupturing, cracking, leakage of tablet contents, etc. Rupture-times were determined by taking the means of successive observation times between which the coatings broke substantially to release the pST. Release of pST was monitored by measuring the UV absorbance of the solution at 276 nm. The mean rupture-time for 8 pellets was determined to be 43±12 hours (1.8±0.5 days) for this combination of coating and matrix. More than 90% of the Zn-rpST was released when the coating was ruptured and was found to be essentially monomeric by Size-Exclusion Chromatography. This experiment was repeated with another set of 8 pellets with a mean percent coating weight of 16.2±0.86. The mean rupture-time was 50±26 hours.

EXAMPLE 2

The procedure in Example 1 was repeated using the following materials to give the results shown:

| Zn-rpST-matrix pellet: | Same as in Example 1 |
|---|---|
| Coating: | Same as in Example 1 |
| Mean % coating weight: | 32.0 ± 1.9. |
| Mean rupture-time: | 110 ± 50 hours |
| Mean % ST released: | 96 ± 9 |

EXAMPLE 3

The procedure in Example 1 was repeated using the following materials to give the results shown:

| Zn-rpST-matrix pellet: | Same as in Example 1 |
|---|---|
| Coating: | Beeswax/Carnauba wax/Mazol 80/20/10 |
| Mean % coating weight: | 32.0 ± 1.1 |
| Mean rupture-time: | 18 ± 1 hours. |
| Mean % ST released: | 84 ± 15 |

EXAMPLE 4

The procedure in Example 1 was repeated using the following materials to give the results shown:

| Protein-matrix pellet: | Bovine serum albumin/Sucrose (50/50 by weight) |
|---|---|
| Coating: | Beeswax/Carnauba wax/Mazol 80/20/2 |
| Mean % coating weight: | 16.7 ± 0.86 |
| Mean rupture-time: | 8.5 ± 1.2 days |
| Mean % protein released: | 92 ± 9 |

EXAMPLE 5

The procedure in Example 1 was repeated using the following materials to give the results shown:

| Protein-matrix pellet: | Lysozyme/Sucrose (50/50 by weight) |
|---|---|
| Coating: | Beeswax/Carnauba wax/Mazol 80/20/2 |
| Mean % coating weight: | 17.1 ± 0.99 |
| Mean rupture-time: | 14.8 ± 2.0 days |
| Mean % protein released: | 67 |

EXAMPLE 6

Pellets of the zinc complex of recombinant porcine somatotropin (Zn-rpST), arginine, and sucrose (1/3/1 parts by weight) were coated with a mixture of beeswax-carnauba wax-Mazol (80:20:10) as described in Example 1. The coated pellets were implanted in pigs and blood samples were taken periodically and analyzed for somatotropin concentration and urea. Elevated levels of somatotropin in the serum, measured using radioimmunoassay (RIA), indicated that the coated pellets had released the protein in the animal. The efficacy of the released protein was measured by the lowering of the Blood Urea Nitrogen (BUN). The experimental design is given in Table 1; the results are shown in Table 2.

Referring to Table 2, the RIA results clearly demonstrate that the coated pellets released the somatotropin later than the uncoated pellets. The BUN results show that the somatotropin released from the coated pellets was efficacious; therefore the coating process did not alter the bioactivity of the protein. The release delay can be altered by modifying the parameters listed above.

EXAMPLE 7

Pellets of the zinc complex of recombinant porcine somatotropin (Zn-rpST), arginine, and sucrose (1/3/1 parts by weight) were coated with a mixture of beeswax-carnauba wax-Mazol as described in Example 1. The coated pellets were implanted in pigs and blood samples were taken periodically and analyzed for somatotropin concentration and urea as described in Example 6. The experimental design is given in Table 3; the results are shown in Table 4.

Referring to Table 4, elevated levels of somatotropin in the serum indicated that the coated pellets had released the protein in the animal. The measured Blood Urea Nitrogen (BUN) values were used to determine the delay-times achieved in the in vivo release of Zn-rpST. The delay-times found were as follows (Mean & Standard Deviation): Treatment 4: 2.6±0.5 days; Treatment 5: 5.7±1.4 days; Treatment 2: <1 day; Treatment 3: Data were too scattered to permit a meaningful determination of mean delay-time.

EXAMPLE 8

Convex pellets (diameter: 4.0 mm) were made from a lactose matrix (Placebos) and from Zn-rpST-matrix (Actives). The composition of Placebos was:

| | |
|---|---|
| Lactose | 19.45 mg |
| Avicel | 29.17 mg |
| Acacia | 0.97 mg |
| Magnesium stearate | 0.39 mg |
| FD & C Blue dye #1 | 0.02 mg |

The composition of the Actives was:

| | |
|---|---|
| Zn-rpST | 10.00 mg |
| L-Arginine | 29.50 mg |
| Sucrose | 10.00 mg |
| Magnesium stearate | 0.50 mg |

A mixture of 1.98 kg of Placebos and 20 grams of Actives was fluidized in a commercial spray-coating machine. A mixture of Stearine (partially hydrogenated cottonseed oil; Durkee Industrial Foods, Cleveland, Ohio), beeswax, and a wetting agent (either polypropylene glycol or Mazol) was prepared by melting all the components together. The molten mixture was then sprayed from the bottom of the spray-coater while the pellets were being fluidized. When the desired amount of the wax coating had been applied on the pellets, the process was stopped to separate the coated Actives. The pellets were evaluated as in Example 1 for % coating weight and rupture-time. The results are shown in Table 5. The levels of the wetting agent are also indicated in Table 5.

Referring to Table 5, it is clear that as the coating weight increased the rupture-time increased. The rupture-time could also be varied by choosing either Mazol or polypropylene glycol.

EXAMPLE 9

Twenty-four barrows were kept in individualized pens and fed a fortified corn-soybean meal diet which met or exceeded current NRC recommendations. On day 0, 10 ml of blood were collected, the animals were weighed and then randomized to one of 3 treatment groups: (1) control (placebo; 0.0 mg of Zn-rpST i.m./pig/day); (2) 2 mg of Zn-rpST i.m./pig/day; and (3) weekly implant with wax pellets containing Zn-rpST.

The third treatment group received one implant weekly for three weeks (day 0, 7 and 14). The implant contained 6 implantable pellets (1 uncoated, 5 wax-coated) having the following composition: ~16 mg Zn-rpST, 16 mg arginine, 16 mg sucrose, ~3 mg polyvinylpyrrolidone and ~0.5 mg magnesium stearate. The average weight of wax coating was 6.8±1.2 mg. The diameter of the pellets was 0.4 cm. The total pST/implant was ~96 mg.

The animals were bled on days 0, 7, 14 and 21 and weighed on days 0, 7, 14, 21, 28 and 35. They were injected or implanted on alternating sides of the neck to avoid repeated irritation of one area. Feed was weighed weekly day 0 to day 35 for feed efficiency calculation. The condition of the pigs were monitored on a daily basis.

The study was conducted as a completely randomized design. The BUN and pST data were analyzed by analysis of covariance and repeated measures with day 0 being used as a covariate (SAS User's Guide: Statistics, Version 5 Ed. SAS Institute, Inc., Cary, N.C. 1985). Feed, weight, weight gain and feed efficiency data were analyzed by analysis of variance. Differences between treatments were compared by the F protected t-test. Means separation was completed using least square difference. The comparisons were: 1) control (placebo) vs treatments 2) day 0 vs days 1 through day 21 within treatment for BUN and pST data. Blood urea nitrogen, animal weight and feed consumed were the data collected to assess pST bioactivity. A depression in BUN and feed efficiency (feed intake/weight gain) indicates an enhancement of animal growth performance. Additionally, serum pST levels were determined to evaluate possible release times of the implanted material. The results showed that there was a significant depression of BUN in treatments 2 and 3 when compared to control values on days 7, 14 and 21 ($P<.05$). Additionally, a time by treatment interaction was observed which further demonstrates the positive effect of treatments 2 and 3 on BUN depression.

The effectiveness of the pST wax-pellet implants was evaluated by the parameters of weight, weight gain, average daily weight gain, feed intake, average daily feed intake and total feed efficiency. These values were calculated and analyzed for three different time periods: treatment (day 0 to day 21), post-treatment (day 21 to day 35), and treatment plus post-treatment (day 0 to day 35). The results are shown in Tables 6, 7, and 8, respectively.

Referring to Table 6, during the treatment period pST implanted animals (treatment 3) outperformed the placebo treated animals. They were higher in average weight, total gain, average daily gain (ADG) and total feed efficiency ($P<.05$). The positive control group, receiving a daily 2 mg pST injection, was significantly higher in total weight gain and in ADG than the implanted group. Therefore, the implanted group's gain was intermediate to positive and negative control groups during the treatment period.

Referring to Table 7, during the post-treatment period, the treatments had no residual effects on any of the growth parameters except for average weight. Daily injected animals were higher in average weight than placebo or pST implanted groups (P<.05). Weight gains made by the implanted group during the treatment period were not enough to sustain a significant difference post-treatment.

Referring to Table 8, the initial effects of treatments 2 and 3 on total feed efficiency were sustained throughout the trial. Although diminished from the ~30% improvement during the treatment period, the overall improvement of pST implanted animals from day 0 to day 35 was 18% above the control values. Serum pST was measured by radioimmunoassay to determine if immunologically active pST was still present in the serum after 1 week post implantation. Implanted animals had elevated (P<.05) pST levels versus the placebo and the daily injected group which had received a 2 mg pST bolus injection 24 hours earlier. Thus, the implant must have released pST within 24 hours of blood sampling. These data demonstrate that pST implanted on days 0, 7 and 14 is being released and is immunologically active 7 days later.

To summarize, the wax-coated implants of pST were biologically active for 7 days. BUN levels were depressed and feed efficiency was enhanced during the treatment period (day 0 to day 21). Total feed efficiency was decreased by pST implants throughout the study. The implanted group performed intermediate to the positive and negative control groups in animal weight and animal weight gain. It appears that the implanted animals were receiving an elevated dose of pST and this dose could adversely affect the animal's feed intake to the detriment of weight gain. Using total feed efficiency as the parameter of growth performance, the pST implants were biologically similar to the 2 mg/pig daily i.m. injection during the treatment period (~30%) and throughout the entire trial (~18%).

Obviously many modifications and variations of the present invention are possible in light of the above teachings. It is therefore to be understood that within the scope of the appended claims the invention may be practiced otherwise than as specifically described.

TABLE 1

| | Description of the Treatments: |
|---|---|
| Treatment 1: | Negative control. |
| # of animals | 4 |
| Treatment 2: | An uncoated, three-layer pellet containing Zn-rpST. |
| # of Animals: | 8 |
| Composition: | A three-layer pellet weighing 130 mg, with the top and bottom layers each containing 15 mg of carnauba wax; the middle layer contains 20 mg Zn-rpST, 59 mg arginine, 20 mg sucrose and 1 mg magnesium stearate; Length: ~0.9 cm; Diameter: 0.4 cm. |
| Administration: | One pellet per animal implanted subcutaneously behind ear on day-0. |
| Treatment 3: | A coated three-layer pellet containing Zn-rpST. |
| # of Animals: | 12 |
| Composition: | A three-layer pellet weighing 130 mg. with the top and bottom layers each containing 15 mg of carnauba wax; the middle layer contains 20 mg Zn-rpST, 59 mg arginine, 20 mg sucrose and 1 mg magnesium stearate; the pellet is coated by dipping twice in molten beeswax-carnauba wax-Mazol mixture (80/20/10) kept at 86° C.; Length: ~1.1 cm; Diameter: 0.5 cm. |
| Administration: | One pellet per animal implanted subcutaneously behind ear on day-0. |

TABLE 2

| | RIA results (ng/ml) | | | | BUN results (mg/dl) | | | |
|---|---|---|---|---|---|---|---|---|
| Treatment | Day 0 | 6 hr | Day 1 | Day 2 | Day 0 | 6 hr | Day 1 | Day 2 |
| 1 | | | | | | | | |
| Mean | 0.93 | 0.40 | 0.0 | 0.38 | 18.1 | 18.5 | 15.1 | 18.9 |
| SEM | 1.11 | 0.80 | 0.0 | 0.75 | 1.7 | 1.0 | 2.3 | 4.8 |
| 2 | | | | | | | | |
| Mean | 0.36 | 72.9 | 9.84 | 3.48 | 16.8 | 16.0 | 6.5 | 8.9 |
| SEM | 0.71 | 17.6 | 9.01 | 6.27 | 3.6 | 3.7 | 1.9 | 3.0 |
| 3 | | | | | | | | |
| Mean | 0.79 | 2.18 | 26.8 | 1.27 | 16.7 | 16.0 | 6.5 | 8.9 |
| SEM | 2.08 | 3.55 | 19.4 | 1.30 | 2.8 | 3.7 | 1.9 | 3.0 |

SEM is the Standard Error of the Mean

TABLE 3

| | Description of the Treatments: |
|---|---|
| Treatment 1: | Negative control. |
| # of animals | 4 |
| Treatment 2: | An uncoated three-layer pellet containing Zn-rpST. |
| # of Animals: | 4 |
| Composition: | A three-layer pellet weighing 130 mg, with the top and bottom layers containing 15 mg carnauba wax each and the middle layer containing 20 mg Zn-rpST, 59 mg arginine, 20 mg sucrose, and 1 mg magnesium stearate; Length: ~0.9 cm; Diameter: ~0.4 cm. |
| Administration: | One pellet per animal implanted subcutaneously. |
| Treatment 3: | A coated three-layer pellet containing Zn-rpST. |
| # of Animals: | 8 |
| Composition: | A pellet as described in Treatment 2 was coated by dipping once in molten beeswax/carnauba wax (80/20) kept at 86° C.; Length: ~1.1 cm; Diameter: ~0.5 cm. |
| Administration: | One pellet per animal implanted subcutaneously. |
| Treatment 4 | A coated three-layer pellet containing Zn-rpST. |
| # of Animals: | 8 |
| Composition: | A pellet as described in Treatment 2 was coated by dipping once in molten beeswax/carnauba wax/Mazol (80/20/2) kept at 86° C.; Length: ~1.1 cm; Diameter: ~0.5 cm. |
| Administration: | One pellet per animal implanted subcutaneously. |
| Treatment 5 | A coated three-layer pellet containing Zn-rpST. |
| # of Animals: | 8 |
| Composition: | A pellet as described in Treatment 2 was coated by dipping twice in molten beeswax/carnauba wax/ Mazol (80/20/2) kept at 86° C.; Length: ~1.1 cm; Diameter: ~0.5 cm. |
| Administration: | One pellet per animal implanted subcutaneously. |

TABLE 4

| | | Comparison of RIA & BUN data[1] | | | | | | | | |
|---|---|---|---|---|---|---|---|---|---|---|
| | | Day | | | | | | | | |
| Trt | Pig # | 2 | 3 | 4 | 5 | 6 | 7 | 8 | 9 | 10 |
| 3 | 940 | 17.3 | 17.4 | 15.3 | 9.6 | 13.1 | 15.2 | | - | |
| | | | 5.9 | 200.9 | 9.5 | 3.2 | | | | |
| | 881 | 19.0 | 16.7 | 19.6 | 19.4 | 21.5 | 16.6 | 15.2 | 9.3 | 10.9 |

TABLE 4-continued

Comparison of RIA & BUN data[1]

| Trt | Pig # | Day 2 | 3 | 4 | 5 | 6 | 7 | 8 | 9 | 10 |
|---|---|---|---|---|---|---|---|---|---|---|
| | | | | | | | 0.0 | 68.0 | 2.1 | 1.0 |
| | 884 | 17.3 | 16.4 | 9.0 | 10.4 | 13.8 | 16.3 | | | |
| | | 1.6 | 0.3 | 17.7 | 2.1 | | | | | |
| | 903 | 20.4 | 19.9 | 22.5 | 20.3 | 21.4 | 22.4 | 20.3 | 10.0 | 13.2 |
| | | | | | | | 1.7 | 1.3 | 17.9 | 0.8 |
| | 806 | 12.8 | 14.6 | 14.4 | 5.9 | 8.5 | 9.5 | 8.3 | 10.7 | 9.4 |
| | | 0.0 | 0.1 | 6.1 | 1.4 | 0.9 | 4.1 | | | |
| | 756 | 12.5 | 13.2 | 14.5 | 8.0 | 10.7 | 18.0 | | | |
| | | 1.0 | 3.5 | 29.5 | 3.9 | | | | | |
| 4 | 860 | 17.9 | 9.5 | 11.1 | 12.2 | 16.2 | 19.0 | | | |
| | | 2.4 | 19.1 | 0.0 | 8.2 | 0.0 | | | | |
| | 886 | 10.7 | 6.9 | 10.4 | 9.9 | 18.2 | | | | |
| | | 139.7 | 3.1 | 3.5 | 0.0 | 1.9 | | | | |
| | 919 | 11.4 | 12.0 | 8.5 | 9.3 | 10.5 | 13.2 | | | |
| | | 3.1 | 53.1 | 0.0 | 0.0 | 6.7 | | | | |
| | 894 | 16.7 | 7.6 | 11.9 | 11.7 | 13.4 | 14.5 | | | |
| | | 1156.0 | 2.5 | 0.0 | 0.0 | 2.3 | | | | |
| | 920 | 18.5 | 13.1 | 11.7 | 16.5 | 17.9 | 18.4 | | | |
| | | 0.9 | 40.4 | 0.0 | 0.0 | 0.0 | | | | |
| | 904 | 15.6 | 11.4 | 10.9 | 10.2 | 14.7 | 13.0 | | | |
| | | 372.0 | 0.0 | 0.0 | 0.0 | 0.0 | | | | |
| | 778 | 18.2 | 9.7 | 9.3 | 12.7 | 15.2 | 16.9 | | | |
| | | 2.1 | 28.2 | 0.0 | 0.0 | 0.9 | | | | |
| | 890 | 17.7 | 10.5 | 10.6 | 12.5 | 16.0 | 15.5 | | | |
| | | 0.7 | 28.9 | 0.0 | 5.5 | 0.0 | | | | |
| 5 | 892 | 18.3 | 17.7 | 18.7 | 20.9 | 9.7 | 9.9 | 12.6 | 14.1 | 12.4 |
| | | | 1.1 | 1.1 | 13.5 | 0.7 | | | | |
| | 874 | 16.3 | 15.2 | 10.5 | 12.1 | 15.0 | 16.9 | 17.8 | 15.0 | 11.9 |
| | | 0.4 | 0.8 | 43.3 | 1.5 | | | | | |
| | 883 | 15.3 | 23.7 | 15.2 | 16.0 | 14.0 | 8.6 | 12.8 | 14.7 | 14.1 |
| | | | | | 1.4 | 102.7 | 3.7 | 3.5 | | |
| | 804 | 14.0 | 15.4 | 12.7 | 11.8 | 11.6 | 9.7 | 11.0 | 12.8 | 14.6 |
| | | | | | 1.8 | 141.5 | 4.9 | 0.7 | | |
| | 809 | 21.9 | 21.6 | 22.5 | 16.5 | 15.5 | 8.9 | 14.7 | 16.8 | 20.9 |
| | | | | | 0.0 | 59.3 | 2.2 | 0.7 | | |
| | 777 | 14.9 | 15.3 | 15.7 | 16.0 | 15.7 | 15.1 | 11.7 | 8.5 | 10.9 |
| | | | | | | 0.0 | 0.0 | 48.6 | 0.8 | |
| | 690 | 14.5 | 16.5 | 15.3 | 17.3 | 12.6 | 7.7 | 13.5 | 14.9 | 14.9 |
| | | | | | 1.1 | 2.1 | 2.9 | 0.4 | | |
| | 880 | 14.7 | 13.0 | 14.3 | 7.7 | 13.5 | 14.0 | | | 17.7 |
| | | | 0.1 | 113.9 | 3.0 | 1.3 | | | | |

[1]BUN data are given in the first line and RIA data on the second line.

TABLE 5

Results from PST-matrix Pellets Spray-Coated with Wax**

| Set # | Coating Type* | Percent Coating Weight | Rupture-time (hours) | % ST released |
|---|---|---|---|---|
| 9 | A | 8.7 ± 0.9 | 9 ± 9 | 106 ± 9 |
| 10 | A | 20.5 ± 2.7 | 164 ± 61 | 98 ± 11 |
| 18 | B | 6.4 ± 1.0 | 2 ± 1 | 110 ± 12 |
| 19 | B | 15.0 ± 2.4 | 162 ± 156 | 103 ± 24 |
| 22 | C | 8.7 ± 1.7 | 5 ± 2 | 92 ± 38 |
| 23 | C | 18.0 ± 2.6 | 117 ± 97 | 100 ± 17 |
| 24 | C | 28.2 ± 2.1 | 180 ± 126 | 106 ± 16 |
| 25 | C | 33.4 ± 3.2 | 306 ± 147 | 107 ± 18 |
| 26 | D | 9.3 ± 2.6 | 4 ± 3 | 108 ± 21 |
| 27 | D | 18.6 ± 3.0 | 30 ± 15 | 101 ± 19 |
| 28 | D | 27.8 ± 3.0 | 106 ± 61 | 105 ± 9 |

*Coating A: Stearine/Beeswax/Polypropylene glycol (80/20/2)
Coating B: Stearine/Beeswax/Polypropylene glycol (80/20/1)
Coating C: Stearine/Beeswax/Mazol (80/20/1)
Coating D: Stearine/Beeswax/Mazol (80/20/2)
** ± Values are Mean ± Standard Deviation

TABLE 6

Treatment Effects on Growth Parameters to Day 21[a]

| | Treatments[b] | | |
|---|---|---|---|
| | 1 | 2 | 3 |
| Average weight (kg) | 73.6$_x$ | 77.6$_y$ | 75.6$_y$ |
| Total gain (kg) | 14.5$_x$ | 19.6$_z$ | 17.5$_y$ |
| ADG (kg/d)[c] | 0.69$_x$ | 0.93$_z$ | 0.83$_y$ |
| Feed intake (kg) | 59.8 | 57.0 | 53.5 |
| ADFI (kg/d)[d] | 2.84 | 2.71 | 2.55 |
| Total F/G[e] | 4.16$_x$ | 2.95$_y$ | 3.07$_y$ |

[a]Growth parameters were totaled and evaluated for the period from day 0 to day 21.
[b]Means with different superscripts (x, y or z) within a parameter are different at the $P < .05$ level.
[c]Average daily gain from day 0 to day 21.
[d]Average daily feed intake from day 0 to day 21.
[e]Total feed efficiency from day 0 to day 21.

TABLE 7

Treatment Effects on Growth Parameters from Day 21 to Day 35[a]

| | Treatments[b] | | |
|---|---|---|---|
| | 1 | 2 | 3 |
| Average weight (kg) | 85.0$_x$ | 90.6$_y$ | 86.9$_x$ |
| Total gain (kg) | 8.15 | 9.26 | 7.11 |
| ADG (kg/d)[c] | 0.58 | 0.66 | 0.51 |
| Feed intake (kg) | 39.9 | 41.6 | 37.9 |
| ADFI (kg/d)[d] | 2.85 | 2.97 | 2.70 |

TABLE 7-continued

Treatment Effects on Growth Parameters from Day 21 to Day 35[a]

| | Treatments[b] | | |
|---|---|---|---|
| | 1 | 2 | 3 |
| Total F/G[e] | 5.99 | 4.55 | 6.35 |

[a] Growth parameters were totaled and evaluated for the period from day 21 to day 35.
[b] Means with different superscripts (x, y or z) within a parameter are different at the $P < .05$ level.
[c] Average daily gain from day 21 to day 35.
[d] Average daily feed intake from day 21 to day 35.
[e] Total feed efficiency from day 21 to day 35.

TABLE 8

Treatment Effects on Growth Parameters to Day 35[a]

| | Treatments[b] | | |
|---|---|---|---|
| | 1 | 2 | 3 |
| Average weight (kg) | 78.1$_x$ | 82.8$_y$ | 80.1$_x$ |
| Total gain (kg) | 22.6$_x$ | 28.8$_y$ | 24.6$_x$ |
| ADG (kg/d)[c] | 0.65$_x$ | 0.82$_y$ | 0.70$_x$ |
| Feed intake (kg) | 99.7 | 98.6 | 91.4 |
| ADFI (kg/d)[d] | 2.85 | 2.82 | 2.61 |
| Total F/G[e] | 4.43$_x$ | 3.43$_z$ | 3.75$_y$ |

[a] Growth parameters were totaled and evaluated for the period from day 0 to day 35.
[b] Means with different superscripts (x, y or z) within a parameter are different at the $P < .05$ level.
[c] Average daily gain from day 0 to day 35.
[d] Average daily feed intake from day 0 to day 35.
[e] Total feed efficiency from day 0 to day 35.

What is claimed is:

1. A controlled release delivery device for implantation in an animal whereby a macromolecular protein is administered to said animal over a prolonged period, said controlled release delivery device comprising:
   a plurality of beadlets having non-uniform rupture times, each of said beadlets comprising a core matrix containing a macromolecular protein and a rupturable wax shell which completely surrounds said core matrix; and
   a water-soluble outer capsule which completely surrounds said plurality of beadlets.

2. The controlled release delivery device of claim 1 wherein said macromolecular proteins are selected from the group consisting of enzymes, enzyme inhibitors, antibodies, antigens, interferons, insulins, prolactins, somatomedins, somatostatins, interleukins, somatocrinins (GRF) and somatotropins.

3. The controlled release delivery device of claim 1 wherein said macromolecular protein is a somatotropin.

4. The controlled release delivery device of claim 3 wherein said somatotropin is selected from the group consisting of human, bovine, ovine, avian, equine, and porcine somatotropins.

5. The controlled release delivery device of claim 3 wherein said somatotropin is porcine somatotropin.

6. The controlled release delivery device of claim 1 wherein said protein comprises from about 1-70% by weight of said beadlet.

7. The controlled release delivery device of claim 1 wherein said core matrix further comprises core agents such as excipients, stabilizers, binders, surfactants, preservatives, or mixtures thereof.

8. The controlled release delivery device of claim 7 wherein said core agents comprises from about 30-99% of said beadlet.

9. The controlled release delivery device of claim 1 wherein said beadlet is a pellet, tablet or microcapsule.

10. The controlled release delivery device of claim 1 wherein said beadlet is a microcapsule.

11. The controlled release delivery device of claim 1 wherein said outer capsule comprises polyvinylpyrrolidine, hydroxypropylmethyl cellulose, gelatin, hydroxypropyl cellulose, or soluble glasses.

12. The controlled release delivery device of claim 1 wherein said outer capsule comprises hydroxypropyl cellulose or gelatin.

13. The controlled release delivery device of claim 3 wherein the rupture times of said beadlets vary uniformly over a period of 1 to 14 days.

14. A method of administering a macromolecular protein to an animal over a prolonged period, comprising:
   implanting a controlled release delivery device in an animal, said controlled release delivery device comprising a plurality of beadlets having non-uniform rupture times, each of said beadlets comprising a core matrix containing a macromolecular protein and a rupturable wax shell which completely surrounds said core matrix; and a water-soluble outer capsule which completely surrounds said plurality of beadlets.

15. The method of claim 14 wherein said macromolecular protein is selected from the group consisting of enzymes, enzyme inhibitors, antibodies, antigens, interferons, insulins, prolactins, somatomedins, somatostatins, interleukins, somatocrinins (GRF) and somatotropins.

16. The method of claim 15 wherein said macromolecular protein is a somatotropin.

17. The method of claim 16 wherein said somatotropin is selected from the group consisting of human, bovine, ovine, avian, equine, and porcine somatotropins.

18. The method of claim 17 wherein said somatotropin is porcine somatotropin.

19. The method of claim 14 wherein controlled release delivery device is implanted subcutaneously.

20. A method for promoting growth and increasing feed utilization efficiency of an animal, comprising:
   implanting a controlled release delivery device in an animal, said controlled release delivery device comprising a plurality of beadlets having non-uniform rupture times, each of said beadlets comprising a core matrix containing a somatotropin and a rupturable wax shell which completely surrounds said core matrix; and a water soluble outer capsule which completely surrounds said plurality of beadlets.

21. The method of claim 20 wherein said somatotropin is selected from the group consisting of human, bovine, ovine, avian, equine, and porcine somatotropins.

22. The method of claim 21 wherein said somatotropin is porcine somatotropin.

23. The method of claim 20 wherein the controlled release delivery device is implanted subcutaneously.

* * * * *